United States Patent [19]

Ikeya et al.

[11] Patent Number: 5,728,391
[45] Date of Patent: Mar. 17, 1998

[54] HYALURONIC ACID AND ITS SALT FOR TREATING SKIN DISEASES

[75] Inventors: Hitoshi Ikeya; Hironoshin Kitagawa, both of Machida, Japan

[73] Assignee: Denki Kagaku Kogyo Kabushiki Kaisha, Tokyo, Japan

[21] Appl. No.: 567,527

[22] Filed: Dec. 5, 1995

[30] Foreign Application Priority Data

Dec. 5, 1994 [JP] Japan .................................... 6-300954
Apr. 25, 1995 [JP] Japan .................................... 7-100904

[51] Int. Cl.$^6$ ...................................................... A61K 7/48
[52] U.S. Cl. ........................ 424/401; 514/54; 514/861; 514/863; 514/969
[58] Field of Search ........................... 424/401; 514/54, 514/861, 863, 969

[56] References Cited

U.S. PATENT DOCUMENTS 4,736,024  4/1988  Della Valle et al. .................. 536/55.3

FOREIGN PATENT DOCUMENTS

92/22585  12/1992  WIPO.
93/16732  9/1993  WIPO.
94/15623  7/1994  WIPO.

OTHER PUBLICATIONS

Skin Research, vol. 28, No. 5, pp. 715–725, Oct. 1986, K. Hakamata, et al., "Clinical Evaluation of Moisturizing Preparations in Patients With Xerotic Dermatoses".

Ann. Opthalmol., vol. 16, No. 9, pp. 823–824, Sep. 1984, V.P. Deluise, et al., "The Use of Topical Healon(R) Tears in the Management of Refractory Dry–Eye Syndrome".

*Primary Examiner*—Jyothsan Venkat
*Attorney, Agent, or Firm*—Oblon, Spivak, McClelland, Maier & Neustadt, P.C.

[57] ABSTRACT

An agent for treating a skin disease selected from the group consisting of a contact dermatitis treating agent, a xerosis senilis treating agent, an asteatosis treating agent, a housewives eczema treating agent, a keratosis treating agent, an eczema chronicum treating agent, a miliaria treating agent and a diaper rash treating agent, which contains hyaluronic acid and/or its salt having an average molecular weight of from 800,000 to 4,000,000, as an active ingredient.

5 Claims, No Drawings

HYALURONIC ACID AND ITS SALT FOR TREATING SKIN DISEASES

The present invention relates to agents for treating skin diseases. More particularly, it relates to agents for treating skin diseases, which contain hyaluronic acid and/or its salt (hereinafter generally referred to as the hyaluronic acid) as an active ingredient and which have excellent moisturizing effects, skin-forming effects, antiinflammatory effects, dry skin treating effects and irritation-relief effects.

Heretofore, for the treatment of skin diseases such as xerosis senilis and miliaria, an adrenocortical steroid agent, an urea ointment, a heparinoid from animal organs, or a vaselin-base ointment such as an azulene ointment, has been used. The adrenocortical steroid agent has strong pharmaceutical effects, but is likely to bring about various side effects. The urea ointment is excellent in the moisturizing effects, but sometimes brings about side effects such as irritation or smarting. The heparinoid from animal organs sometimes brings about a contact dermatitis as a side effect. Therefore, theses agents have had problems from the viewpoint of safety. On the other hand, the vaselin-base ointment such as an azulene ointment presents an unpleasant feeling such as a sticky feeling, upon application, and at the same time, a foreign matter such as dust is likely to deposit thereon. Thus, such an ointment has had a problem with respect to the feeling upon application.

From these viewpoints, there has been no treating agent for skin diseases, which is capable of presenting fully satisfactory curing effects against the above-mentioned diseases.

On the other hand, hyaluronic acid is a natural component contained in the skin, and it is free from side effects and has a high moisturizing effect without irritation and presents a moist feeling when applied to the skin. Therefore, it is widely used for cosmetics, and it is used also as pharmaceuticals in the field of ophthalmology or orthopedics.

Further, with respect to skin diseases, Japanese Unexamined Patent Publication No. 285038/1986 discloses that a hyaluronic acid having a relatively low molecular weight with an average molecular weight of from about 30,000 to 730,000, has wound curing effects against e.g. decubitus, burn and ulcer.

However, curing effects against skin diseases, such as xerosis senilis and miliaria have not been known.

The present inventors have conducted extensive studies and as a result, have found that an agent for treating a skin disease containing, as an active ingredient, the hyaluronic acid having an average molecular weight of from 800,000 to 4,000,000, brings about little side effects, is excellent in the feeling upon application and has an excellent effect for treating skin diseases, as is distinguished from the conventional treating agents for skin diseases. The present invention has been accomplished on the basis of this discovery.

Thus, the present invention provides an agent, for treating a skin disease selected from the group consisting of a contact dermatitis treating agent, a xerosis senilis treating agent, an asteatosis treating agent, a housewives eczema treating agent, a keratosis treating agent, an eczema chronicum treating agent, a miliaria treating agent and a diaper rash treating agent, which contains hyaluronic acid and/or its salt having an average molecular weight of from 800,000 to 4,000,000, as an active ingredient.

Further, the present invention provides also use of hyaluronic acid and/or its salt having an average molecular weight of from 800,000 to 4,000,000, for the manufacture of an agent for treating a skin disease selected from the group consisting of a contact dermatitis treating agent, a xerosis senilis treating agent, an asteatosis treating agent, a housewives eczema treating agent, a keratosis treating agent, an eczema chronicum treating agent, a miliaria treating agent and a diaper rash treating agent.

Now, the present invention will be described in detail.

The agent for treating a skin disease of the present invention is useful for the treatment of e.g. a contact dermatitis, particularly a nonallergic contact dermatitis, xerosis senilis, asteatosis, housewives eczema, eczema chronicum such as neurodermitis, miliaria, diaper rash, or a keratosis such as keratodermia tylodes palmaris progressive, keratosis palmaris et plantaris, ichthyosis, lichen pilaris, psoriasis or pityriasis rosea Gilbert.

Hyaluronic acid can be obtained from an extract of e.g. a cockscomb, a viterous body or an umbilical code, or from a culture of certain bacteria such as a hyaluronic acid-producing microorganism of Genus *streptcoccus*. Hyaluronic acid can be used for the present invention irrespective of its origin. However, hyaluronic acid obtainable from the culture of a hyaluronic acid-producing microorganism is preferred, since one having a high molecular weight can be obtained in high purity. Essentially, hyaluronic acid is one of mucopolysaccharides, which is widely distributed in connective tissues of mammals including human beings, and it is present mostly in the synovial fluid, the viterous body, the skin or the umbilical code. In the skin, it contributes to moisturizing, provision of elasticity and prevention of bacterial infection.

Hyaluronic acid presents no antigenicity in each of tests for an anaphylaxis reaction, an intradermal reaction, a corneal reaction and a PCA reaction using guinea pigs, mice and rabbits (Kougo Nakagawa et al., JAPANESE PHARMACOLOGY & THERAPEUTICS, 12, 141, 1984; JAPANESE PHARMACOLOGY & THERAPEUTICS, 12, 151, 1984), and it is highly safe so that it can be used as a pharmaceutical in the field of ophthalmology or orthopedics.

For the agent for treating a skin disease of the present invention, hyaluronic acid may be used in the form of an acid, or in the form of a hyaluronic acid salt. As the salt, an alkali metal salt such as a sodium or potassium salt, an alkaline earth metal salt such as a magnesium or calcium salt, may be mentioned. In the present invention, a sodium salt is particularly preferred.

With hyaluronic acid, the one having a small molecular weight provides no adequate moisturizing effect (Perfume Association Journal 12,50–59, 1988), and the one having a molecular weight of 4,000,000 or larger tends to be highly viscous, whereby formulation will be difficult.

Accordingly, the average molecular weight of the hyaluronic acid to be used for the agent for treating a skin disease of the present invention is usually within a range of from 800,000 to 4,000,000, preferably from 1,000,000 to 3,000,000.

The concentration of the hyaluronic acid for the agent for treating a skin disease of the present invention is preferably from 0.001 to 3.0 w/v %, more preferably from 0.05 to 1.0 w/v %. If the concentration of the hyaluronic acid is less than 0.001 w/v %, no adequate treating effects tend to be obtained, and if it exceeds 3.0 w/v %, it tends to be difficult to completely dissolve it in a solvent such as water, whereby it tends to be difficult to obtain a uniform solution.

The agent for treating a skin disease of the present invention contains the hyaluronic acid. However, its formulation is not particularly limited, and it may be formulated into an optional form such as an emulsifiable ointment, a water-soluble ointment, a lotion, or an aqueous solution. It may be formulated in accordance with conventional formulation methods for usual agents for treatment of skin diseases. For preparation of the formulation, components commonly used for agents for treating skin diseases may be optionally incorporated, which include e.g. an oily base-component such as petrolatum or liquid paraffin, an emulsifier such as macrogol or lauromacrogol, a preservative such as a parahydroxy benzoate ester or salicylic acid, a moisturizing agent such as glycerol or sorbitol, a stabilizer, and a perfume.

Now, the present invention will be described in further detail with reference to Examples. However, it should be understood that the present invention is by no means restricted to such specific Examples.

EXAMPLE 1

Composition 1

| Sodium hyaluronate (molecular weight: 1,900,000) | 2 g |
|---|---|
| White petrolatum | 188 g |
| Stearyl alcohol | 150 g |
| Propylene glycol | 90 g |
| Polyoxyethylene hydrogenated castor oil | 30 g |
| Glyceryl monostearate | 8 g |
| Methyl parahydroxy benzoate | 1 g |
| Propyl parahydroxy benzoate | 1 g |
| Purified water | 530 g |
| Total | 1000 g |

Sodium hyaluronate was added to 530 g of purified water and dissolved with stirring at room temperature. Added to this solution was a solution having methyl parahydroxy benzoate and propyl parahydroxy benzoate dissolved in propylene glycol, if necessary, under heating. The mixture was heated to about 75° C. and added to a uniform liquid previously prepared by stirring a mixture comprising white petrolatum, stearyl alcohol, polyoxyethylene hydrogenated castor oil and glyceryl monostearate at about 75° C. The mixture was stirred to obtain an emulsion. Then, it was cooled and thoroughly stirred until it was solidified, to obtain a hydrophilic ointment.

The hydrophilic ointment thus prepared was applied to a diseased portion of a patient of nonallergic contact dermatitis from 3 to 5 times per day for 2 weeks, whereby an improvement in the symptom was observed.

COMPARATIVE EXAMPLE 1

Composition 2

| Sodium hyaluronate (molecular weight: 600,000) | 2 g |
|---|---|
| White petrolatum | 188 g |
| Stearyl alcohol | 150 g |
| Propylene glycol | 90 g |
| Polyoxyethylene hydrogenated castor oil | 30 g |
| Glyceryl monostearate | 8 g |
| Methyl parahydroxy benzoate | 1 g |
| Propyl parahydroxy benzoate | 1 g |
| Purified water | 530 g |
| Total | 1000 g |

Sodium hyaluronate was added to 530 g of purified water and dissolved with stirring at room temperature. Added thereto was a solution having methyl parahydroxy benzoate and propyl parahydroxy benzoate dissolved in propylene glycol, if necessary, under heating. The mixture was heated to about 75° C. and added to a uniform liquid which was previously prepared by stirring a mixture comprising white petrolatum, stearyl alcohol, polyoxyethylene hydrogenated castor oil and glyceryl monostearate at about 75° C. The mixture was stirred to obtain an emulsion. Then, it was cooled and thoroughly stirred until it was solidified, to obtain a hydrophilic ointment.

The hydrophilic ointment thus prepared was applied to a diseased portion of a patient of nonallergic contact dermatitis from 3 to 5 times per day for 2 weeks for treatment, whereby no improvement in the symptom was observed.

EXAMPLE 2

The same treating agent as used in Example 1, was applied to a diseased portion of each of two patients of xerosis senilis and two patients of asteatosis from 3 to 5 times per day for treatment, whereby the symptom was substantially reduced in one to two weeks. Further, no irritation to the skin was observed.

EXAMPLE 3

Composition 3

| White petrolatum | 400 g |
|---|---|
| Cetanol | 200 g |
| White beeswax | 50 g |
| Lauromacrogol | 5 g |
| Sorbitan sesquioleate | 50 g |
| Ethyl parahydroxy benzoate | 1 g |
| Butyl parahydroxy benzoate | 1 g |
| Sodium hyaluronate (molecular weight: 1,900,000) | 2 g |
| Deionized water | 291 g |
| Total | 1000 g |

Sodium hyaluronate was added to 291 g of purified water and dissolved with stirring at room temperature. To this solution, ethyl parahydroxy benzoate and butyl parahydroxy benzoate were added and dissolved under heating. This solution was kept at 80° C. and added to a uniform liquid which was previously prepared by stirring a mixture comprising white petrolatum, cetanol, white beeswax, lauromacrogol and sorbitan sesquioleate at 75° C. The mixture was stirred to obtain an emulsion. Then, the emulsion was cooled and thoroughly stirred until it was solidified, to obtain an absorptive ointment.

The absorptive ointment thus prepared was applied to each of seven patients of housewives eczema from 3 to 5 times per day for treatment, whereby reduction of the pain was observed with six patients in two to three weeks.

EXAMPLE 4

The same treating agent as used in Example 2 was applied to five patients of keratosis from 3 to 5 times per day for treatment, whereby an improvement in the symptom was observed with four patients in two to three weeks.

EXAMPLE 5

Composition 4

| Sodium hyaluronate (molecular weight: 1,900,000) | 3 g |
|---|---|
| Purified water | 997 g |
| Total | 1000 g |

Sodium hyaluronate was added to 997 g of purified water and dissolved with stirring at room temperature to obtain an aqueous hyaluronic acid solution.

The aqueous solution thus prepared was applied to each of five infants showing a symptom of miliaria or diaper rash, at the time of taking bath, after cleaning or at the time of changing the diaper, for treatment, whereby an improvement in the symptom was observed in all of them in two to three weeks.

EXAMPLE 6

Composition 5

| | |
|---|---|
| Sodium hyaluronate (molecular weight: 1,400,000) | 5 g |
| White petrolatum | 188 g |
| Stearyl alcohol | 150 g |
| Propylene glycol | 90 g |
| Polyoxyethylene hydrogenated castor oil | 30 g |
| Glyceryl monostearate | 8 g |
| Methyl parahydroxy benzoate | 1 g |
| Propyl parahydroxy benzoate | 1 g |
| Purified water | 527 g |
| Total | 1000 g |

Sodium hyaluronate was added to 527 g of purified water and dissolved with stirring at room temperature. Added thereto was a solution having methyl parahydroxy benzoate and propyl parahydroxy benzoate dissolved in propylene glycol, if necessary, under heating. The mixture was heated to about 75° C. and added to a uniform liquid which was previously prepared by stirring a mixture comprising white petrolatum, stearyl alcohol, polyoxyethylene hydrogenated castor oil and glyceryl monostearate at about 75° C. The mixture was stirred to obtain an emulsion. Then, it was cooled and thoroughly stirred until it was solidified, to obtain a hydrophilic ointment.

The hydrophilic ointment thus prepared was applied to a diseased portion of two patients of eczema chronicum from 2 to 3 times per day for one month for treatment. Until the application of the hydrophilic ointment, one patient had used a zinc oxide ointment, and the other had used a urea ointment, whereby no improvement had been observed in the symptom. By the treatment with the hydrophilic ointment of the present invention, an improvement was observed in the dryness and in the itching feeling with both of them. With each patient, the hydrophilic ointment of the present invention exhibited better effects than the conventional drug which was commonly used.

As described in the foregoing, the agent for treating a skin disease of the present invention is excellent in the feeling on application and presents little irritation to the skin, and it is useful for treatment of various skin diseases such as contact dermatitis, xerosis senilis, asteatosis, housewives eczema, keratosis, eczema chronicum, miliaria and diaper rash.

We claim:

1. A process for treating a skin disease selected from the group consisting of xerosis senilis, asteatosis, keratodermia tylodes palmaris progressive, keratosis palmaris et plantaris, ichthyosis, lichen pilaris, pityriasis rosea Gilbert, and miliaria, which comprises applying to the skin a skin-treating effective amount of at least one of hyaluronic acid and its salt, having an average molecular weight of from 800,000 to 4,000,000.

2. The process of claim 1, wherein the average molecular weight is from 1,000,000 to 3,000,000.

3. The process of claim 1, wherein the skin disease is xerosis senilis.

4. The process of claim 1, wherein the skin disease is asteatosis.

5. The process of claim 1, wherein the skin disease is miliaria.

* * * * *